United States Patent
Jacob et al.

(10) Patent No.: US 10,121,817 B2
(45) Date of Patent: Nov. 6, 2018

(54) RADIATION DETECTOR FOR USE AS AN IMAGE INTENSIFIER

(71) Applicant: General Electric Company, Schenectady, NY (US)

(72) Inventors: Biju Jacob, Schenectady, NY (US); James Zhengshe Liu, Salt Lake City, UT (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 94 days.

(21) Appl. No.: 14/973,417

(22) Filed: Dec. 17, 2015

(65) Prior Publication Data

US 2017/0179186 A1  Jun. 22, 2017

(51) Int. Cl.
*G01N 23/04* (2018.01)
*H05G 1/64* (2006.01)
(Continued)

(52) U.S. Cl.
CPC ..... *H01L 27/14663* (2013.01); *G01N 23/043* (2013.01); *G01T 1/247* (2013.01)

(58) Field of Classification Search
CPC ......... H01L 27/14603; H01L 27/14607; H01L 27/14663; H01L 27/14687; H01L 31/0272; H01L 31/0296; H01L 31/02966; H01L 31/0304; H01L 31/032; H01L 27/14632; H01L 31/1055; H01L 27/14634; H01L 27/14689; H01L 2924/0002; H01L 27/14609; H01L 27/14621; H01L 27/14627; H01L 27/1463; H01L 27/14636; H04N 5/3696; H04N 5/3742; H04N 5/376; H04N 5/378; A61B 6/46; A61B 6/06; A61B 6/4035; A61B 6/4233; A61B 6/469; A61B 6/5205; A61B 6/5258; A61B 6/542; A61B 6/545; A61B 6/583; A61B 6/585; A61B 6/487; A61B 6/025; A61B 6/08; A61B 6/12; A61B 6/4291; A61B 6/488; A61B 6/541; A61B 6/587; A61B 5/06; A61B 6/032; A61B 6/4028; A61B 6/42;
(Continued)

(56) References Cited

U.S. PATENT DOCUMENTS 2,512,146 A * 6/1950 Fulmer .................. H01J 40/04
                                                  220/2.3 R
3,794,874 A * 2/1974 Mulder .................. C07C 45/71
                                                  313/148

(Continued)

OTHER PUBLICATIONS

"Exxim's Fluoroscopy CMOS Detector Applications", Exxim Computing Corporation, http://www.exxim-cc.com/technology_xraysensors.htm, 2006.

(Continued)

*Primary Examiner* — Irakli Kiknadze
(74) *Attorney, Agent, or Firm* — GE Global Patent Operation; Pabitra Chakrabarti

(57) ABSTRACT

A flat panel detector is provided having a circular active area. The flat panel detector is built using complementary metal-oxide-semiconductor (CMOS) tiles. In one implementation, the flat panel detector having a circular active area can be used as a replacement for a conventional image intensifier, including an image intensifier used in a fluoroscopy system.

19 Claims, 2 Drawing Sheets

(51) Int. Cl.
*H01L 27/146* (2006.01)
*G01T 1/24* (2006.01)

(58) Field of Classification Search
CPC ............ A61B 6/4216; A61B 6/4225; G06T
2207/10116; G06T 2207/20104; G06T
2207/0208; G06T 2210/41; G06T 3/40;
H01J 29/385; H01J 9/12; H01J 29/92;
H01J 31/501; H01J 31/505; H01J 1/34;
H01J 2201/3421; H01J 2231/50036; H01J
2231/50063; H01J 29/863; H01J 40/02;
G21K 4/00; G21K 2004/06; C09K
11/7733; C09K 11/08; C09K 11/615;
G01N 23/043; G01T 1/247
USPC ............ 378/19, 62, 98.8, 189; 250/370.11,
250/370.13, 379.09
See application file for complete search history.

(56) References Cited

U.S. PATENT DOCUMENTS

| | | | |
|---|---|---|---|
| 3,838,273 A * | 9/1974 | Cusano | G21K 4/00 250/214 VT |
| 4,213,055 A * | 7/1980 | Schrijvers | H01J 31/501 250/214 VT |
| 6,895,077 B2 | 5/2005 | Karellas et al. | |
| 7,009,646 B1 | 3/2006 | Fossum et al. | |
| 7,129,462 B2 | 10/2006 | Hogan et al. | |
| 2006/0192087 A1 | 8/2006 | Kuszpet et al. | |
| 2007/0023617 A1 * | 2/2007 | Thomas | H01J 31/507 250/214 VT |
| 2010/0140487 A1 | 6/2010 | Barrett et al. | |
| 2011/0260608 A1 * | 10/2011 | Rosine | H01J 31/507 313/532 |
| 2011/0297839 A1 * | 12/2011 | Berauer | G01T 1/2018 250/370.11 |
| 2014/0063502 A1 | 3/2014 | Jiang et al. | |
| 2015/0146847 A1 | 5/2015 | Liu | |
| 2015/0303228 A1 * | 10/2015 | Rohr | H01L 27/14603 250/366 |
| 2015/0313558 A1 * | 11/2015 | Melman | G21K 1/04 378/62 |

OTHER PUBLICATIONS

Tamaki et al., "Development of 4-Sides Buttable CdTe-ASIC Hybrid Module for X-ray Flat Panel Detector", IEEE Transactions on Nuclear Science, vol. 56, Issue 4, pp. 1-4, Aug. 2009.

Tran, "A Four-Side-Buttable Tiling Scheme for a Near Real-Time Digital Radiography Detector for Medical Applications", The Third Solid State Systems Symposium-VLSI and Semiconductor Related Technologies, 11 pages, 2014.

* cited by examiner

RADIATION DETECTOR FOR USE AS AN IMAGE INTENSIFIER

BACKGROUND

The subject matter disclosed herein relates to X-ray imaging and, in particular, to the fabrication and use of a tiled radiation detector as a radiological imaging unit consisting of an X-ray image intensifier and a CCD (charge-coupled device) camera. For the sake of simplicity, the term image intensifier, when used herein, refers to the entire radiological imaging unit.

Non-invasive imaging technologies allow images of the internal structures or features of a patient or object to be obtained without performing an invasive procedure on the patient or object. In particular, such non-invasive imaging technologies rely on various physical principles, such as the differential transmission of X-rays through the target volume or the reflection of acoustic waves, to acquire data and to construct images or otherwise represent the observed internal features of the patient or object.

For example, in fluoroscopy and other X-ray based imaging technologies, X-ray radiation is directed toward a subject, typically a patient in a medical diagnostic application, a package or baggage in a security screening application, or a fabricated component in an industrial quality control or inspection application. A portion of the radiation impacts a detector where the image data is collected and used in an image generation process. In the images produced by such systems, it may be possible to identify and examine the internal structures and organs within a patient's body, objects within a package or container, or defects (e.g., cracks) within a fabricated component. In certain contexts, such as fluoroscopy applications used in support of interventional or navigation procedures, low-dose X-rays may be acquired at a high frame rate over an extended period to provide real-time image data that may be used to guide or navigate a tool within a patient.

In the context of fluoroscopy, an image intensifier is conventionally used to detect the transmitted X-rays and to generate useful signals for image generation. Such conventional image intensifiers are generally provided as bulky, cylindrical devices having either a 6", 9" or 12" diameter active area. The image intensifier converts X-rays to images often in substantially real time.

One obstacle to replacing image intensifiers in legacy systems with newer radiation detector technology is the form factor of the image intensifiers in the installed base of devices. In particular, in existing fluoroscopic installations, the image intensifiers are typically provided as cylindrical components, and thus have a round cross section. In contrast, flat panel X-ray detectors are conventionally square or rectangular in form factor which corresponds to the row-column matrix readout of the pixel arrays. Thus, replacing the existing circular cross-section image intensifiers with square or rectangular flat panel detectors is not a straight-forward operation if it is desired to maintain the existing cylindrical form factor.

BRIEF DESCRIPTION

In one aspect, a radiation detector is provided. In accordance with this aspect, the radiation detector includes a plurality of complementary metal-oxide-semiconductor (CMOS) tiles. The CMOS tiles are configured to abut adjacent CMOS tiles on four sides to form a light sensing panel having a sensing area with a boundary between a circular active area used for imaging and a circular enclosure.

In a further aspect, an X-ray imaging system is provided. In accordance with this aspect, the X-ray imaging system includes: an X-ray source configured to emit a beam of X-rays having a circular cross-section through an imaging volume, a flat panel detector, and an image processing unit. The flat panel detector includes a plurality of CMOS tiles that form a light sensing panel and having a circular active area. The circular active area can be exposed to radiation to generate signals from which images can be reconstructed. The image processing unit applies a digital mask to mask out the value of the pixels outside the active area yielding the circular shape images.

In an additional aspect, a method of emulating an image intensifier using a flat panel detector is provided. In accordance with this method, interpreting system commands intended for the image intensifier to commands for the flat panel detector and responses back from the flat panel detector to the system are provided. In addition, pixels of a flat panel detector are binned to correspond to different magnification modes of the image intensifier. Finally a digital mask is applied to the obtained image to produce the circular shape image intensifier type image.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
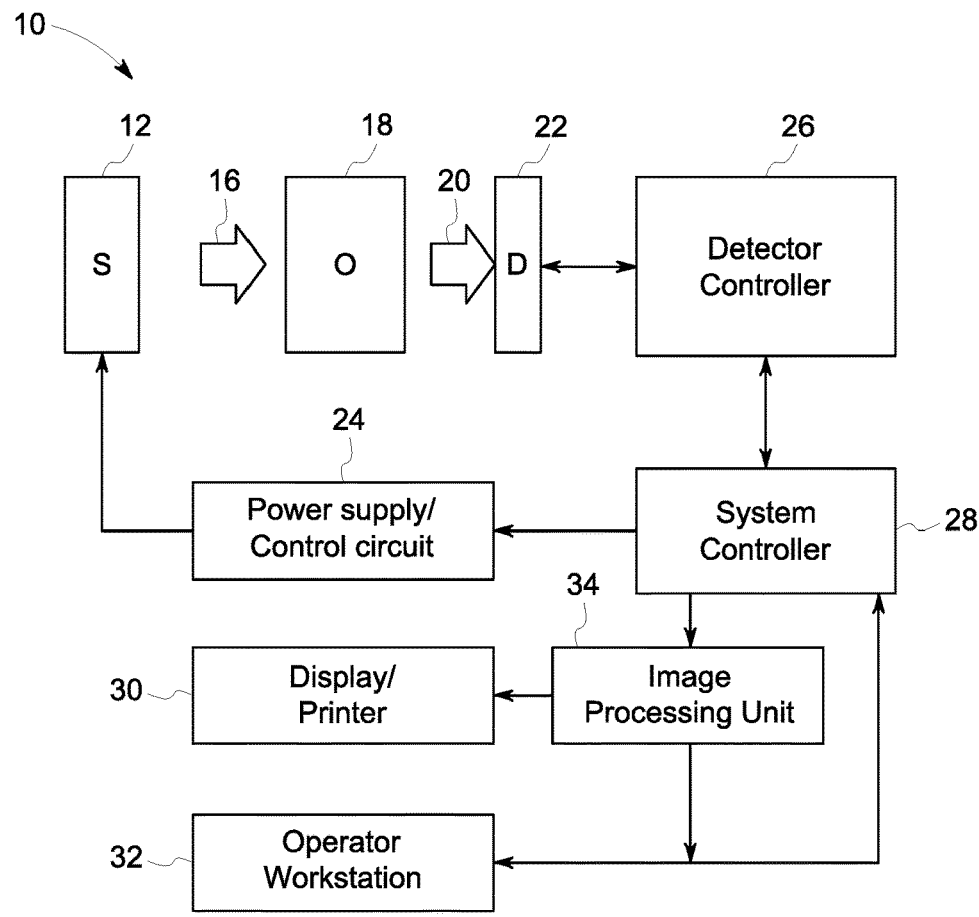
FIG. 1 is a diagrammatical view of an imaging system for use in producing images in accordance with aspects of the present disclosure.

One or more specific implementations will be described below. In an effort to provide a concise description of these implementations, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements.

While the following discussion is generally provided in the context of medical imaging, it should be appreciated that the present techniques are not limited to such medical contexts. Indeed, any examples and explanations provided in such a medical context is only to facilitate explanation by providing instances of real-world implementations and applications. However, the present approaches may also be utilized in other contexts, such as the non-destructive inspection of manufactured parts or goods (i.e., quality control or quality review applications), and/or the non-invasive inspection of packages, boxes, luggage, and so forth (i.e., security or screening applications).

X-ray panels for medical and industrial inspection conventionally are made using amorphous silicon (a-Si) technology, despite the limitations associated with a-Si. However, in some applications there is a need for imager panels with higher resolution and lower electronic noise than may be achievable with a-Si technology. In particular, X-ray detectors based on crystalline silicon (c-Si) technology, such as those employing CMOS formed from c-Si, may outperform traditional a-Si based X-ray detectors in various ways.

However, traditional disadvantages of using c-Si include higher cost and size and shape limitations due to the use of silicon wafers to fabricate c-Si devices. In practice, c-Si imagers made using silicon wafers may be tiled together to form a detector panel of useful size. However, such tiling arrangements introduce complexities in the electrical interconnection arrangements needed to operate (e.g., readout) such a detector panel and may be difficult or impractical to implement in practice. Further, tiled or otherwise, conventional flat panel detectors are typically formed as rectangular or square structures, which makes arrangement of the electrical interconnections at the edges a straight-forward proposition. Such rectangular shapes and side-based interconnection arrangements are not suitable for fabricating certain shapes of detectors, such as circular detectors that may be used in place of conventional image intensifiers. Further, interfaces for flat panel detectors, and the images generated by them, may differ from those associated with conventional image intensifiers, making straightforward substitution of flat panel detectors for image intensifiers an unsuitable option.

As discussed herein, approaches are discussed for overcoming the limitations typically associated with c-Si fabrication techniques to form light imager panels having circular active area cross-sections by tiling together smaller imager tiles. As used herein, the active area refers to that region of the detector or detector panel used by the system to generate images (i.e., to that portion of the detector from which acquired signals are processed to generate an image). In certain disclosed implementations, the active area of the described flat panel detector is circular and corresponds in shape and size to the active area of conventional image intensifiers. Conversely, as used herein, the sensing area of a flat panel detector corresponds to that area on which imagers or CMOS tiles are placed, even though some portions of these tiles (e.g., the irregular edges along the perimeter) may not be read out or, if read out, may not contribute useful information. For example, portions of the perimeter of the sensing area may be digitally and/or structurally masked so as to provide a circular active area. Thus, the sensing area as discussed herein is larger than the active area and has a perimeter that lies between the circumference of the circular active area and an external boundary, such as an edge of the light imager panel and/or an image intensifier enclosure, which may also be circular.

Detector panels fabricated in accordance with these approaches may be used in place of image intensifiers in certain X-ray imaging contexts, such as fluoroscopy. As discussed herein, approaches employing CMOS technology are described that address these needs. With this in mind, the present approaches use smaller (e.g. 2.0 cm to 5 cm on a side) four-side buttable CMOS tiles (i.e., light imagers), which may be arranged to build panels having an active area comparable in shape and size to current image intensifiers. Use of CMOS tiles that are smaller in size than conventional tiles allow improved yields and this potentially lowers the panel cost.

Therefore, as discussed herein, different methods for assembling circular X-ray panels using four-side buttable digital CMOS tiles are provided. In certain implementations, readout electronics may be integrated with each CMOS tile, such that data is read out and converted to digital signals at the tile-level, and signal acquired from each tile is in the form of digital signals, typically representative of groups of pixels on a given tile.

With the preceding in mind, and turning now to the drawings, FIG. 1 illustrates diagrammatically an imaging system 10 for acquiring and processing image data using a detector fabricated as discussed herein. In the illustrated embodiment, system 10 is a digital X-ray system, such as a fluoroscopy system, designed both to acquire original image data and to process the image data for display. The imaging system 10 may be a stationary or mobile X-ray system. In the embodiment illustrated in FIG. 1, imaging system 10 includes a source of X-ray radiation 12 that emits a beam or stream of radiation 16 into a region in which an object or subject 18 is positioned. The beam of radiation may be collimated or shaped to have a specified cross-section, such as a circular cross-section corresponding to the size and shape of an active area of the detector 22. A portion of the radiation 20 passes through or around the subject and impacts a digital X-ray detector, represented generally at reference numeral 22. The detector 22 may be portable or permanently mounted to the system 10. In certain embodiments, a scintillator of the detector 22 may convert the incident X-ray photons to lower energy photons which are detected by a light imager panel as discussed herein, i.e., a light imager panel comprised of tiled CMOS tiles or imagers. Electrical signals are generated in response to the detected photons at the light imager panel and these signals are processed to reconstruct an image of the features within the object or subject. In certain implementations, the detector 22 may be a flat panel detector that has been placed in (e.g., substituted for) an image intensifier in an existing image system installation, such as by retrofitting the flat panel detector and related interconnections into an image intensifier enclosure.

As discussed herein, the detector array 22 may be formed from a plurality of tiled CMOS imagers positioned between a substrate and a scintillator, each separately defining an array of detector elements (e.g., pixels). Each detector element produces an electrical signal that represents the intensity of the X-ray beam incident at the position of the detector element when the beam strikes the detector 22. In one embodiment, each tiled imager includes separate readout electronics configured for reading out pixels on the respective CMOS tile and providing separate respective digital outputs corresponding to groups (e.g., sub-arrays) of pixels on the respective tile. That is, readout occurs at two separate levels of abstraction, with pixel readout occurring at each tile and tile readout occurring at the detector level. Digital signals representative of groups of pixels on each respective tile are acquired and processed to generate one or more scan datasets.

Source 12 is controlled by a power supply/control circuit 24 which furnishes both power and control signals for examination sequences. Moreover, detector 22 includes a detector controller 26 (e.g., control circuitry) which commands acquisition of the signals generated in the detector 22. Detector controller 26 may also execute various signal processing and filtration functions, such as for initial adjustment of dynamic ranges, interleaving of digital image data, and so forth. Both power supply/control circuit 24 and detector controller 26 are responsive to signals from a system controller 28. In general, system controller 28 commands operation of the imaging system to execute examination protocols and to process acquired image data, such as at image processing unit 34. In the present context, system controller 28 may also include signal processing circuitry and one or more data storage structures, such as optical memory devices, magnetic memory devices, or solid-state memory devices, for storing programs and routines executed by a processor of the system 10 to carry out various functionalities. In one embodiment, a programmed computer system may be provided with hardware, circuitry, firmware, and/or software for performing the functions attributed to one or more of the power supply/control circuit 24, the detector controller 26, the image processing unit 34, and/or the system controller 28.

In the embodiment illustrated in FIG. 1, system controller 28 is linked to an image processing unit 34 which in turn conveys reconstructed images to at least one output device, such as a display or printer as indicated at reference numeral 30. The output device may include standard or special purpose monitors and associated processing circuitry. One or more operator workstations 32 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, cloud-based network, and so forth.

In an implementation where the detector 22 is a flat panel detector 22 that has been installed in a system 10 previously equipped with an image intensifier, certain interface modifications may be made so as to replicate the control and outputs of the image intensifier. As will be appreciated, though certain examples may be provided by way of simplifying explanation, such interface provisions may be made at various locations within the system 10 to achieve the same effect. Thus, while examples may be made which reference the detector 22, controller 26, system controller 28, and/or image processing unit 34, it should be appreciated that such examples are provided for illustration only. Indeed, the described interface enhancements may be achieved in other ways or using other components while remaining within the presently contemplated scope of the disclosure.

By way of example, interface electronics within one or more of the detector 22, the detector controller 26, system controller 28, and/or image processing unit 34 may be provided to interpret commands (e.g., system commands) to the detector 22 from the system. In this manner, a command generated by the system controller 28 for an image intensifier is interpreted or modified so as to have the same or a similar effect at the flat panel detector 22. By way of example, commands for an image intensifier related to adjustments to an image intensifier field of view, image rotation, gain, and so forth may be interpreted so as to achieve the same or a comparable effect at the detector 22. For example, as discussed in greater detail below, commands related to different magnification modes (e.g., fields of view) of an image intensifier may be interpreted or modified so as to command different binning and/or interpolation operations at the detector 22 so as to achieve a comparable magnification or field of view.

Similarly, data acquired from the flat panel detector 22 may be interpreted or modified so as to conform to data that would be acquired from an image intensifier so that downstream components of the system 10 can continue to operate as if an image intensifier were still present. By way of example, an image processing unit 34 of the system 20 may be programmed or otherwise configured so as to digitally mask an image generated by the detector 22 to a circular shape, thus conforming to the circular images generated by an image intensifier.

To facilitate and simplify explanation, only certain of the components that may be present in an imaging system 10 are described. Other components or functionalities may be present however. By way of example, structural components, such as a gantry or C-arm, may be present on which one or both of the source 12 or detector 22 may be mounted. Such mounting structures may allow data to be acquired over an angular range during an examination. Similarly, various rotational positioning subsystems (such as for control rotation of the source 12 and detector 22) and/or linear positioning subsystems (such as for linearly translating the objet or patient 18 during an examination) may also be present, in practice, the imaging system 10 may be any suitable X-ray based imaging system, including, but not limited to, conventional radiography systems, CT imaging systems, tomosynthesis systems, C-arm systems, fluoroscopy systems, mammography systems, dual- or multiple-energy systems, navigational or interventional imaging systems, and so forth. In addition, the imaging system 10 may be used in conjunction with, and/or may communicate with, a navigational or interventional system for imaging a tool or instrument within a patient during a procedure.

Keeping in mind the operation of the system 10 and, specifically, the detector 22 discussed above with respect to FIG. 1, the present approaches provide for the fabrication of detector panel assemblies from CMOS imager tiles that may abut other CMOS imager tiles on all four-sides within a two-dimensional plane (i.e., the plane of the tile). In certain such implementations, the data and control interconnections to each tile may be provided above or below the plane of the tile, where the plane is understood to correspond to the long dimensions of the tile (e.g., 2.0 cm×2.0 cm, 5 cm×5 cm, and so forth), which allows a given tile to abut other tiles on all four sides (i.e., four-side buttable).

Figure 2:
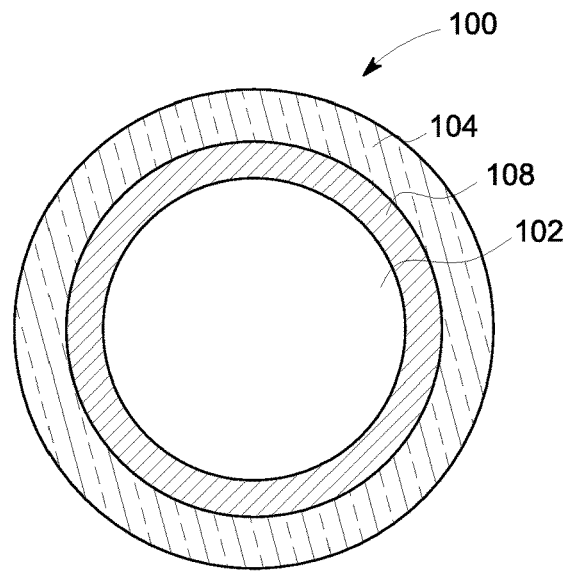
FIG. 2 depicts a top down view of a prior art image intensifier showing the circular active area.

With the preceding comments in mind, a top-down view of a conventional image intensifier 100 is shown in FIG. 2. In this example, the image intensifier 100 has an active area 102, i.e., the area, which generates signals used for image reconstruction in response to incident X-rays, that is approximately 8.4" in diameter (215 mm) (i.e., approximately an 8.4" field-of-view) in the depicted example. A circumferential bumper 104, such as a rubber or other shock absorbent material providing mechanical protection, is also depicted which has an outer diameter of approximately 14" inches (355 mm). In addition, a non-active area ring 108 having an outer diameter of approximately 11.25" (285 mm) is provided between the active area 102 and bumper 104. The ring 108, if present, may be provided for regulatory or other purposes and constitutes a region in which X-ray incidence does not generate image signal. It should be appreciated that all measurements are provided by way of non-limiting examples, here the example of a conventional 9" image intensifier. As will be appreciated, other dimensions and intensifiers sizes are possible, such as those corresponding to a conventional 6" or 12" active area image intensifier or to image intensifiers of different sizes and shapes.

Figure 3:
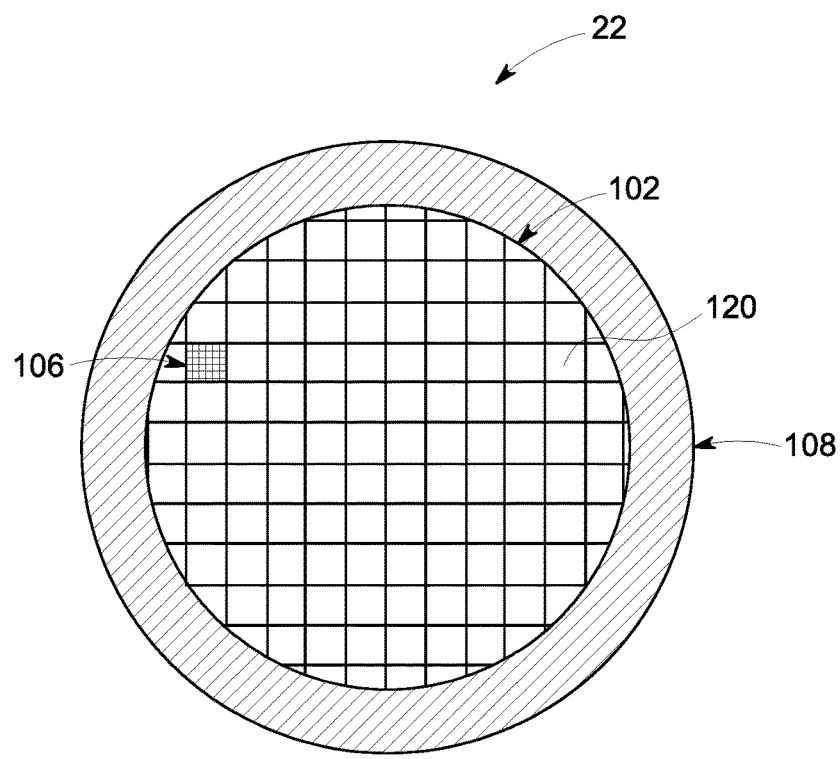
FIG. 3 depicts a top down view of a portion of a flat panel detector array masked to have a circular active area, in accordance with aspects of the present disclosure.
Figure 4:
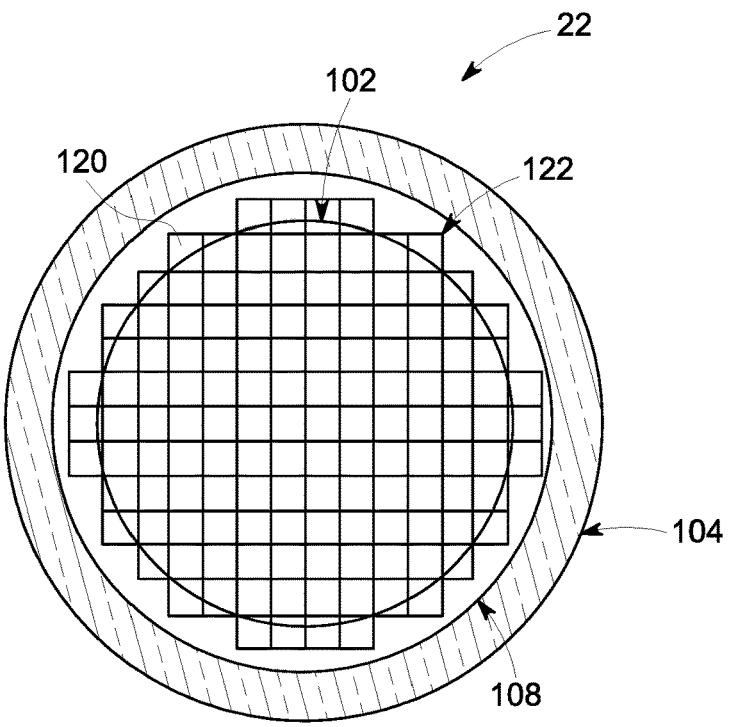
FIG. 4 depicts a further top down view of a portion of a flat panel detector array showing both the circular active area and the larger sensing area positioned between the active area and image intensifier enclosure, in accordance with aspects of the present disclosure.

Thus, as shown in FIG. 2, a conventional image intensifier 100 has a circular active area 102 upon which X-rays are directed to generate an X-ray image, such as a series of fluoroscopic images in video form. Turning to FIGS. 3 and 4, two different views of a flat panel detector 22 formed from rectangular or square CMOS tiles 120 and having a form factor and active area comparable to that of the conventional image intensifier 100 are shown. FIG. 3 depicts a circular active area 102 formed using CMOS tiles 120 and surrounded by inactive (i.e., non-imaging) ring 108, which may help the active area 102 of FIGS. 3 and 4 as a circular active area as may be present on an image intensifier. Thus, FIG. 3 depicts the active portion of the detector 22 as it will appear to from an external view, which, as shown, corresponds in shape and size to the active area provided by a conventional image intensifier even though rectangular or square CMOS tiles 120 are employed. FIG. 4 provides a similar view, but with the circular active area 102 shown in outline online only (i.e., by a single, circular line) so that the underlying configuration of CMOS tiles 120 forming the overall sensing area 122 is visible. FIG. 4 also depicts the bumper 104 which may be present on image intensifier enclosures. As will be appreciated from this view, the circular active area 102 is smaller than the overall sensing area 122 defined by the full extent of the CMOS tiles 120, which themselves do not define an actual circle. As a result, the perimeter or outer bound of the sensing area 122 lies between the boundary of the active area 102 and one or more of the edge of the light image panel or some feature of the circular enclosure, such as an image intensifier enclosure, such as the bumper 104 or structural feature of the enclosure. By way of example, in the depicted view, the outer boundary of the sensing area 122 lies between concentric circles formed respectively by the edge of the active area 102 and the image intensifier enclosure. As shown in FIGS. 3 and 4, therefore, the active area 102 of the detector 22 may be characterized or described as being within two or more concentric circles defined by other features, such as active area 102 and the ring 108 or bumper 104. The circular boundary of the active area 102 may be defined by structural features and/or by a digital mask applied by the system 10 (such as by image processing unit 34) so as to correspond to the circular active area of an image intensifier.

As noted above, the CMOS tiles 120 are, in the depicted example, four-side (i.e., square or rectangular) buttable CMOS tiles 120 that each include an array of pixels 106 (which, to simplify are shown for only one tile 120 of FIG. 3). Each CMOS tile 120 may each include readout electronics (including analog-to-digital signal conversion circuitry), such that the output signals acquired from each tile 120 are digital signals corresponding to grouped pixel outputs on the respective CMOS tile 120. Electrical connections to the readout electronics may be accessible on the bottom of the CMOS tiles 120, thus allowing the tiles 120 to abut other tiles 120 on all four sides (i.e., four-side buttable), as shown.

In a given detector panel 22, there may be any suitable number of CMOS tiles 120. CMOS tiles 120 may, in certain implementations, be 2.0 cm×2.0 cm, 5 cm ×5 cm, and so forth, in the dimensions defining the plane of the tile and may be 200 µm to 700 µm thick. By way of example, each CMOS tile 120 may measure 500 pixels×500 pixels, with each pixel in turn measuring 50 µm×50 m or 100 µm×100 µm.

The CMOS tiles 120 are oriented and spaced precisely on an underlying substrate, such as using automated or machine placement, based on the image quality requirements of the application for which the detector 22 will be used. Typically the spacing and orientation of the tiles 120 will also be determined so that the geometry stays stable during the thermal life-cycle of the panel. Typically the physical spacing between the adjacent tiles 120 is controlled so that the butting gap between tiles is less than a pixel pitch across, i.e., approximately 1 line of data, and in one implementation is 50 µm or less. In this manner, less than one line of data is lost due to the presence of the gap.

As noted above, the detectors 22 having a circular active area 102 may be shaped and sized so as to correspond to, and be interchangeable with, a conventional image intensifier, such as an image intensifier used in a fluoroscopic imaging context. For example, the detector 22 may be sized and shaped so as to fit within a mechanical enclosure otherwise used to hold an image intensifier or within a smaller enclosure. Thus, the detector 22 may be provided as a replacement kit for replacing an image intensifier in an existing or legacy system with a flat panel detector. In such an implementation, the interface electronics (which may be implemented in the detector 22 itself, the detector controller 26, the system controller 28, the image processing unit 34, and/or via the combined interaction of these components) for the detector 22 may correspond to that provided by the image intensifier being replaced so as to facilitate the upgrade. That is commands generated for an image intensifier may be interpreted or converted so as to command a corresponding operation or setting of the detector 22 while outputs of the detector 22 may be interpreted or converted so as to correspond to the outputs of an image intensifier.

Thus, the interface provided for the detector 22 (such as via the interaction of one or both of the detector controller 26 or the system controller 28 with the detector 22 or by the detector 22 itself) may be configured to provide the same functionality as that provided by the image intensifier, including having the same or comparable field of view, image rotation, gain, and so forth. By way of example, functionalities may be incorporated into the interface that automatically apply image rotation via interpolation prior to sending to the downstream system components and/or provide digital-to-analog conversion at the level of the detector 22 or tiles 120 prior to sending to the downstream system components. In addition, the provided interface may provide for a video level indicator (in fluoroscopic contexts) to mimic the camera iris present in an image intensifier context and/or digital gain configured to correspond to the conventional camera gain of an image intensifier.

In addition, the interface for the detector 22, when used to replace an image intensifier may provide for different fields of view or levels of magnification based on the readout operation, such as a full diameter (i.e., "unmagnified") field of view and one or more magnified fields of view, such as a fields of view corresponding to three-quarters, two-thirds, or half of the full field of view diameter. By way of example, in one embodiment, use of readout circuitry including binning control circuitry integrated with each CMOS tile may be employed to provide different levels of magnification or fields of view. In an example of one such implementation, a CMOS tiled flat panel detector 22 configured to replace a 12" image intensifier and having 50 µm pixel pitch may be provided with three different magnification modes, a first mode employing 4×4 pixel binning, a second mode employing 3×3 pixel binning, and a third mode employing 2×2 binning. In a further example, a CMOS tiled flat panel detector 22 configured to replace a 9" image intensifier and having 50 µm pixel pitch may be provided with three different magnification modes, a first mode employing 3×3 pixel binning, a second mode employing 2×2 pixel binning, and a third mode employing interpolation. In an additional example, a CMOS tiled flat panel detector 22 configured to replace a 6" image intensifier and having 50 µm pixel pitch may be provided with three different magnification modes, a first mode employing 2×2 pixel binning, a second mode employing interpolation, and a third mode using native 1×1 resolution. In this manner, the various magnification modes often available for use with an image intensifier may be replicated in the interface for a CMOS tile flat panel detector 22 employing integrated readout circuitry at the tile level with binning control.

Technical effects of the invention include providing a flat panel detector employing CMOS tiles that serves as a replacement for an image intensifier. In certain implementations, the flat panel detector has an active area that is circular.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A flat panel radiation detector, comprising:
a plurality of complementary metal-oxide-semiconductor (CMOS) tiles arranged to form a light sensing panel comprising a circular active area; and
a non-imaging ring disposed on the light sensing panel, wherein the circular active area of the light sensing panel is defined by an inner boundary of the non-imaging ring, and
wherein the non-imaging ring is disposed on the light sensing panel such that portions of outer CMOS tiles of the plurality of CMOS tiles are masked by the non-imaging ring so as to define the circular active area.

2. The flat panel radiation detector of claim 1, further comprising a circular bumper disposed outside the non-imaging ring.

3. The flat panel radiation detector of claim 1, wherein the circular active area corresponds to a region of the light sensing panel that generates signals, and wherein the signals are employed to reconstruct images.

4. The flat panel radiation detector of claim 1, wherein the radiation detector is configured to fit within an image intensifier enclosure.

5. The flat panel radiation detector of claim 1, wherein each CMOS tile of the plurality of CMOS tiles comprises sides measuring between about 2.0 cm to about 5.0 cm, and wherein each CMOS tile of the plurality of CMOS tiles is between about 200 µm to about 700 µm thick.

6. The flat panel radiation detector of claim 1, further comprising readout electronics corresponding to each CMOS tile of the plurality of CMOS tiles, wherein the readout electronics corresponding to each CMOS tile of the plurality of CMOS tiles is configured to readout groups or sub-arrays of pixels from among a respective array of pixels on each CMOS tile and to output a digital signal.

7. The flat panel radiation detector of claim 6, wherein the readout electronics corresponding to each CMOS tile of the plurality of CMOS tiles is configured to selectively bin the readout of pixels on each CMOS tile to correspond to different magnification levels.

8. The flat panel radiation detector of claim 1, wherein the plurality of CMOS tiles is arranged in a non-rectangular shape.

9. The flat panel radiation detector of claim 1, further comprising an interface configured to provide fields of view, image rotation, and gain corresponding to the flat panel radiation detector.

10. An X-ray imaging system, comprising:
an X-ray source configured to emit a beam of X-rays through an imaging volume, wherein the emitted beam of X-rays comprises a circular cross-section;
a flat panel detector comprising:
a plurality of complementary metal-oxide-semiconductor (CMOS) tiles arranged to form a light sensing panel comprising a circular active area;
a non-imaging ring disposed on the light sensing panel, wherein the circular active area of the light sensing panel is defined by an inner boundary of the non-imaging ring, and
wherein the non-imaging ring is disposed on the light sensing panel such that portions of outer CMOS tiles of the plurality of CMOS tiles are masked by the non-imaging ring so as to define the circular active area; and
an image processing unit, wherein the image processing unit is configured to apply a digital mask to an image produced by the flat panel detector to generate a circular shaped X-ray image.

11. The X-ray imaging system of claim 10, wherein the X-ray imaging system is a fluoroscopy system.

12. The X-ray imaging system of claim 10, wherein the flat panel detector is fitted into an enclosure configured to hold an image intensifier.

13. The X-ray imaging system of claim 10, wherein a CMOS tile of the plurality of CMOS tiles is disposed such that the CMOS tile is surrounded by adjacent CMOS tiles on four sides.

14. The X-ray imaging system of claim 10, wherein each CMOS tile of the plurality of CMOS tiles comprises integrated readout electronics configured to output digital data signals to the image processing unit.

15. The X-ray imaging system of claim 14, wherein the integrated readout electronics corresponding to each CMOS tile of the plurality of CMOS tiles is configured to readout groups or sub-arrays of pixels from among a respective array of pixels on each CMOS tile and to output the digital data signals based on the readout of the groups or sub-arrays of pixels.

16. The X-ray imaging system of claim 14, wherein the integrated readout electronics is configured to selectively bin the readout of pixels on a corresponding CMOS tile to correspond to different magnification levels.

17. A method of emulating an image intensifier using a flat panel detector, comprising:
- interpreting system commands intended for the image intensifier to commands for the flat panel detector and responses back from the flat panel detector corresponding to those from the image intensifier, wherein the flat panel detector comprises a plurality of complementary metal-oxide-semiconductor (CMOS) tiles arranged to form a light sensing panel comprising a circular active area and a non-imaging ring disposed on the light sensing panel, wherein the circular active area of the light sensing panel is defined by an inner boundary of the non-imaging ring, and wherein the non-imaging ring is disposed on the light sensing panel such that portions of outer CMOS tiles of the plurality of CMOS tiles are masked by the non-imaging ring so as to define the circular active area; and
- masking an image generated by the responses from the flat panel detector to a circular shape image corresponding to images generated by the image intensifier.

18. The method of claim 17, further comprising applying interpolation to correspond to additional magnification modes not supported by binning pixels.

19. The method of claim 17, wherein interpreting the system commands comprises performing pixel binning at the flat panel detector to correspond to different imaging magnification modes provided by the image intensifier.

* * * * *